(12) United States Patent
Jaumard et al.

(10) Patent No.: US 10,245,046 B2
(45) Date of Patent: Apr. 2, 2019

(54) ASSEMBLY FOR A TIBIAL CUT GUIDE

(71) Applicant: Zimmer, Inc., Warsaw, IN (US)

(72) Inventors: Nicolas V. Jaumard, Warsaw, IN (US); Josh Betts, Dublin, OH (US); James S. Collins, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 219 days.

(21) Appl. No.: 15/341,306

(22) Filed: Nov. 2, 2016

(65) Prior Publication Data

US 2017/0135708 A1    May 18, 2017

Related U.S. Application Data

(60) Provisional application No. 62/254,474, filed on Nov. 12, 2015.

(51) Int. Cl.
*A61B 17/17* (2006.01)
*A61B 17/00* (2006.01)

(52) U.S. Cl.
CPC ...... *A61B 17/1764* (2013.01); *A61B 2017/00477* (2013.01); *A61B 2017/00862* (2013.01)

(58) Field of Classification Search
CPC .............................. A61B 17/17; A61B 17/1764
See application file for complete search history.

(56) References Cited

U.S. PATENT DOCUMENTS

| | | | | |
|---|---|---|---|---|
| 5,628,750 A | * | 5/1997 | Whitlock | A61B 17/157 606/86 R |
| 7,641,663 B2 | | 1/2010 | Hodorek | |

(Continued)

FOREIGN PATENT DOCUMENTS

| | | |
|---|---|---|
| CN | 107920825 | 4/2018 |
| GB | 2480846 | 12/2011 |

(Continued)

OTHER PUBLICATIONS

"International Application Serial No. PCT/US2017/050957, Invitation to Pay Additional Fees and Partial Search Report dated Nov. 21, 2017", 13 pgs.
"International Application Serial No. PCT/US2017/050957, International Search Report dated Jan. 24, 2018", 6 pgs.
"International Application Serial No. PCT/US2017/050957, Written Opinion dated Jan. 24, 2018", 10 pgs.

(Continued)

*Primary Examiner* — Christopher Beccia
(74) *Attorney, Agent, or Firm* — Schwegman Lundberg & Woessner, P.A.

(57) ABSTRACT

Systems and apparatuses including apparatuses that can be used in a knee replacement procedure are disclosed. According to one example, an assembly for a knee replacement surgery is disclosed. The assembly can comprise an adjustment member, a carrier assembly, a posterior slope housing assembly, and a boom. The carrier assembly can be configured to selectively couple with the adjustment member such that the carrier assembly is moveable relative to the adjustment member to a desired position. The posterior slope housing assembly can be connected to the adjustment member and can be configured to pivot the adjustment member relative to a portion of the posterior slope housing and a tibia. The boom can be coupled to the posterior slope housing assembly and can be configured to couple with a mounting component to mount the posterior slope housing assembly, the carrier assembly and the adjustment member relative to the tibia.

16 Claims, 11 Drawing Sheets

(56) References Cited

U.S. PATENT DOCUMENTS

| | | | |
|---|---|---|---|
| 8,317,797 B2* | 11/2012 | Rasmussen | A61B 17/025 606/88 |
| 8,758,354 B2* | 6/2014 | Habegger | A61B 17/157 606/88 |
| 2006/0184173 A1* | 8/2006 | Collazo | A61B 17/155 606/62 |
| 2007/0233138 A1 | 10/2007 | Figueroa et al. | |
| 2012/0179266 A1 | 7/2012 | Collazo | |
| 2013/0204260 A1 | 8/2013 | Dietzel et al. | |
| 2014/0066934 A1 | 3/2014 | Deirmengian et al. | |
| 2015/0196308 A1 | 7/2015 | Wilkinson et al. | |
| 2015/0342742 A1 | 12/2015 | Ferro et al. | |
| 2016/0367271 A1 | 12/2016 | Jones et al. | |
| 2018/0070960 A1 | 3/2018 | Branscome et al. | |
| 2018/0070961 A1 | 3/2018 | Branscome et al. | |

FOREIGN PATENT DOCUMENTS

| | | |
|---|---|---|
| WO | WO-2008091358 A1 | 7/2008 |
| WO | 2012158604 | 11/2012 |
| WO | WO-2013063375 A1 | 5/2013 |
| WO | 2016205454 | 12/2016 |
| WO | 2018052843 | 3/2018 |

OTHER PUBLICATIONS

"International Application Serial No. PCT/US2016/037765, International Search Report dated Nov. 21, 2016", 5 pgs.

"International Application Serial No. PCT/US2016/037765, Written Opinion dated Nov. 21, 2016", 8 pgs.

"International Application Serial No. PCT/US2016/037765, Invitation to Pay Additional Fees and Partial Search Report dated Sep. 9, 2016", 7 pgs.

"U.S. Appl. No. 15/184,016, Non Final Office Action dated May 2, 2018", 16 pgs.

"U.S. Appl. No. 15/184,016, Response filed Aug. 8, 2018 to Non Final Office Action dated May 2, 2018", 15 pgs.

"U.S. Appl. No. 15/184,016, Advisory Action dated Nov. 5, 2018", 3 pgs.

"U.S. Appl. No. 15/184,016, Final Office Action dated Aug. 29, 2018", 15 pgs.

"U.S. Appl. No. 15/184,016, Response filed Oct. 29, 2018 to Final Office Action dated Aug. 29, 2018", 15 pgs.

"U.S. Appl. No. 15/266,311, Non Final Office Action dated Aug. 30, 2018", 10 pgs.

"European Application Serial No. 16732186.8, Response filed Sep. 3, 2018 to Office Action dated Feb. 20, 2018", 16 pgs.

"U.S. Appl. No. 15/266,311, Response filed Nov. 26, 2018 to Non Final Office Action dated Aug. 30, 2018", 10 pgs.

* cited by examiner

ASSEMBLY FOR A TIBIAL CUT GUIDE

CLAIM OF PRIORITY

This application claims the benefit of U.S. Provisional Patent Application Ser. No. 62/254,474, filed on Nov. 12, 2015, the benefit of priority of which is claimed hereby, and which is incorporated by reference herein in its entirety.

FIELD

The present subject matter relates to orthopedic procedures and, more particularly, to an assembly that can aid in bone resection for knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

The present inventors recognize the need for an intramedullary (IM) cutting rig assembly that can be used to quickly and accurately position (with regard to proximal-distal location, anterior-posterior location, and/or posterior slope angle) a tibial cut guide for removal of the articular surfaces of the tibia. The inventors recognize the assembly can include subassembly components such as a posterior slope housing assembly that can quickly and accurately adjust the posterior slope angle and an anterior-posterior position of the tibia cut guide. Further, the inventors recognize the need for a carrier subassembly that can be used in combination with a member (e.g., a rod) to adjust a proximal-distal position of the tibial cut guide. The carrier subassembly can be configured to allow for coupling of the tibial cut guide with the carrier subassembly in a quick and efficient manner. One or more connections between subassemblies disclosed can be "quick-connect" or "quick-release" in nature to facilitate quick and accurate assembly, disassembly, positioning, and repositioning of the various subassemblies and cut guide. According to further examples, the posterior slope housing subassembly can be configured to allow for adjustment of the posterior slope angle of the tibial cut guide relative to the tibia without having to swap out the tibial cut guide for another tibial cut guide (e.g., swap a cut guide with a cut slot predefining 3° of posterior slope angle for a cut guide with a cut slot predefining 5° of posterior slope angle). Thus, only one tibial cut guide need be utilized with the assembly. Additionally, the posterior slope housing subassembly can be configured to allow for non-discrete (non-incremental) adjustment of the posterior slope angle of the tibial cut guide relative to the tibia. This facilitates continuous and smooth adjustment of the posterior slope angle and allows for virtually any desired posterior slope angle (e.g., 2°, 2.1°, 2.2°, and so forth) to be achieved. Thus, the intramedullary (IM) cutting rig assembly can allow for resection of the tibia with minimal amounts of adjustment and/or swapping of the tibial cut guide.

To further illustrate the apparatuses and systems disclosed herein, the following non-limiting examples are provided:

In Example 1, an assembly for a knee replacement surgery can comprise an adjustment member, a carrier assembly, a posterior slope housing assembly, and a boom. The carrier assembly can be configured to selectively couple with the adjustment member such that the carrier assembly is moveable relative to the adjustment member to a desired position. The posterior slope housing assembly can be connected to the adjustment member and can be configured to pivot the adjustment member relative to a portion of the posterior slope housing and a tibia. The boom can be coupled to the posterior slope housing assembly and can be configured to couple with a mounting component to mount the posterior slope housing assembly, the carrier assembly and the adjustment member relative to the tibia.

In Example 2, the system of Example 1, wherein the adjustment member can comprise a T-shaped rod having threading along at least one surface thereof, and wherein the carrier assembly can include an engagement mechanism comprising a threaded knob configured to selectively engage the threading.

In Example 3, the system of Example 2, wherein the threaded knob can be displaced via a spring force to engage the threading, and the engagement mechanism can include a button configured to be actuated to overcome the spring force and facilitate movement of the carrier assembly along the adjustment member.

In Example 4, the system of any one or any combination of Examples 1 to 3, wherein the carrier assembly can include a body component moveable relative to a housing, the body component can be configured to engage with the cut guide, and wherein the carrier assembly can include a mechanism that couples and locks the body component with the housing.

In Example 5, the system of any one or any combination of Examples 1 to 4, wherein the posterior slope housing assembly can be pivotally connected to the adjustment member along a proximal end portion thereof, the proximal end portion can be configured to mate with a moveable connector of the posterior slope housing assembly.

In Example 6, the system of Example 5, wherein the posterior slope housing assembly can include a knob configured to rotate a screw, and the connector can be configured to translate on the screw to rotate the proximal end portion of the adjustment member and facilitate pivoting of the adjustment member relative to the tibia to adjust the posterior slope angle.

In Example 7, the system of Example 6, can further comprise a counter-nut configured to engage the posterior slope housing assembly to lock a position of the screw and connector, and wherein the posterior slope housing assembly and adjustment member can include visual indicia including incremental value indicia down to or less than 1° indicating the posterior slope angle.

In Example 8, the system of Example 6, wherein rotation of the screw and translation of the connector can facilitate a non-discrete adjustment of the posterior slope angle.

In Example 9, the system of any one or any combination of Examples 1 to 8, wherein the boom can comprise a T-shaped rod having threading along at least one surface thereof, and wherein the posterior slope housing assembly can include an adjustment mechanism that comprises a button that is configured to be depressible to facilitate adjustment of the posterior slope housing assembly and releasable to engage the threading.

In Example 10, the system of any one or any combination of Examples 1 to 9, wherein the adjustment member can be configured to provide a track for proximal-distal movement of the carrier assembly, and wherein the boom can be configured to provide a track for anterior-posterior movement of the posterior slope housing assembly.

In Example 11, an assembly for a knee replacement surgery can comprise an adjustment member, a carrier assembly, a posterior slope housing assembly, and a boom. The carrier assembly can be configured to selectively couple with the adjustment member such that the carrier assembly can be moveable relative to the adjustment member to a desired position. The posterior slope housing assembly can be connected to the adjustment member and can be configured to pivot the adjustment member relative to a portion of the posterior slope housing and a tibia. The boom can be coupled to the posterior slope housing assembly and can be configured to couple with a mounting component to mount the posterior slope housing assembly, the carrier assembly and the adjustment member relative to the tibia.

In Example 12, the assembly of Example 11, wherein the adjustment member can comprise a T-shaped rod having threading along at least one surface thereof, and wherein the carrier assembly can include an engagement mechanism that includes a threaded knob configured to selectively engage the threading.

In Example 13, the assembly of Example 12, wherein the threaded knob can be displaced via a spring force to engage the threading, and the engagement mechanism includes a button that when actuated overcomes the spring force to facilitate movement of the carrier assembly along the adjustment member.

In Example 14, the assembly of any one or any combination of Examples 11 to 13, wherein the carrier assembly can include a body component moveable relative to a housing, the body component can be configured to engage with a cut guide to seat the cut guide, and wherein the carrier assembly can include a mechanism that couples and locks the body component with the housing.

In Example 15, the assembly of any one or any combination of Examples 11 to 14, wherein the posterior slope housing assembly can be pivotally connected to the adjustment member along a proximal end portion thereof, the proximal end portion can be configured to mate with a moveable key connector of the posterior slope housing assembly.

In Example 16, the system of Example 15, wherein the posterior slope housing assembly can be configured to rotate a screw, and the key connector can be configured to translate on the screw to move the proximal end portion of the adjustment member and facilitate pivoting of the adjustment member relative to the tibia to adjust the posterior slope angle.

In Example 17, the system of Example 16, can further comprise a counter-nut configured to engage the posterior slope housing assembly to lock a position of the screw and key connector, and wherein the posterior slope housing and adjustment member can include visual indicia including incremental value indicia down to or less than 1° indicating the posterior slope angle.

In Example 18, the system of Example 16, wherein rotation of the screw and translation of the key connector can facilitate a non-discrete adjustment of the posterior slope angle.

In Example 19, the system of any one or any combination of Examples 11 to 18, wherein the boom can comprise a I-shaped rod having threading along at least one surface thereof, and wherein the posterior slope housing assembly can include an adjustment mechanism that comprises a button that can be configured to be depressible to facilitate adjustment of the posterior slope housing assembly and releasable to engage the threading.

In Example 20, the system of any one or any combination of Examples 11 to 19, wherein the adjustment member can provide a track for proximal-distal movement of the carrier assembly, and wherein the boom can provide a track for anterior-posterior movement of the posterior slope housing assembly.

In Example 21, an assembly for a knee replacement surgery can comprise an adjustment member, a carrier assembly, a posterior slope housing assembly, and a boom. The carrier assembly can he configured to selectively couple with the adjustment member such that the carrier assembly can be moveable relative to the adjustment member to a desired position. The posterior slope housing assembly can be connected to the adjustment member and can be configured to pivot the member relative to a portion of the posterior slope housing and a tibia. The posterior slope housing assembly can be pivotally connected to the adjustment member along a proximal end portion thereof, the proximal end portion can be configured to mate with a key connector. The posterior slope housing assembly can be configured to rotate a screw, and the key connector can be configured to translate relative to the screw to rotate the proximal end portion of the adjustment member and facilitate pivoting of the adjustment member relative to the tibia to adjust the posterior slope angle. The boom can be coupled to the posterior slope housing assembly and can be configured to couple with a tool that can be insertable into an intramedullary canal of the tibia.

In Example 22, the assembly of Example 21, wherein rotation of the screw and translation of the key connector can facilitate a non-discrete adjustment of the posterior slope angle.

In Example 23, the apparatuses and systems of any one or any combination of Examples 1 to 22 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for knee replacement procedures. For example, the present application discloses an intramedullary (IM) cutting rig assembly that can position a tibial cut guide for removal of the articular surfaces of the tibia.

Figure 1:
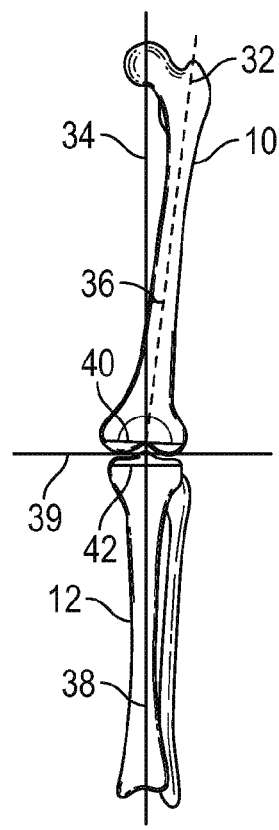
FIG. 1 is a front elevation view of a tibia and a femur showing axes of the knee joint according to an example of the present application.

FIG. 1 illustrates various axes of the lower limb in the frontal plane. Axes can be defined for each segment of the lower limb. For example, a femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane. Likewise, a tibia 12 has a mechanical axis 38 coinciding generally with its intramedullary canal. The mechanical axis 38 of the tibia 12 runs from the center of the knee to the center of the ankle. The transverse axis, or joint line 39, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

A distal femoral cut can be made perpendicular to the femoral axes 32, 34 in the sagittal plane. A proximal tibial resection is typically cut to match the natural posterior slope of the proximal tibia in the sagittal plane, relative to the mechanical axes 34, 38. The amount of posterior to anterior slope (also referred to herein as posterior slope angle) relative perpendicular to the mechanical axes 34, 38 varies in the patient population but is on the order of 2° to 7°. The distance between the distal femoral cut and proximal tibial cut along the mechanical axes 34, 38 is the extension gap. Other cuts may be made depending on the components that are to be implanted and the type of procedure performed.

As used herein, "proximal" refers to a direction generally toward the torso of a patient, and "distal" refers to the opposite direction of proximal, i.e., away from the torso of a patient. "Anterior" refers to a direction generally facing away from the patient, i.e. toward the surgeon performing the surgery, and "posterior" refers to the opposite direction of anterior, i.e., toward the front (anterior) of a patient or knee. In the context of the assembly such as those disclosed herein, such directions correspond to the orientation of the assembly when in use (i.e. when mounted to or adjacent the patient in an operable position to assist in making desired resections), such that a proximal portion of the assembly is that portion which will ordinarily be closest to the torso of the patient, the anterior portion closest to the surgeon, the posterior portion generally closest to the anterior portion of the patient's knee, etc.

Figure 2A:
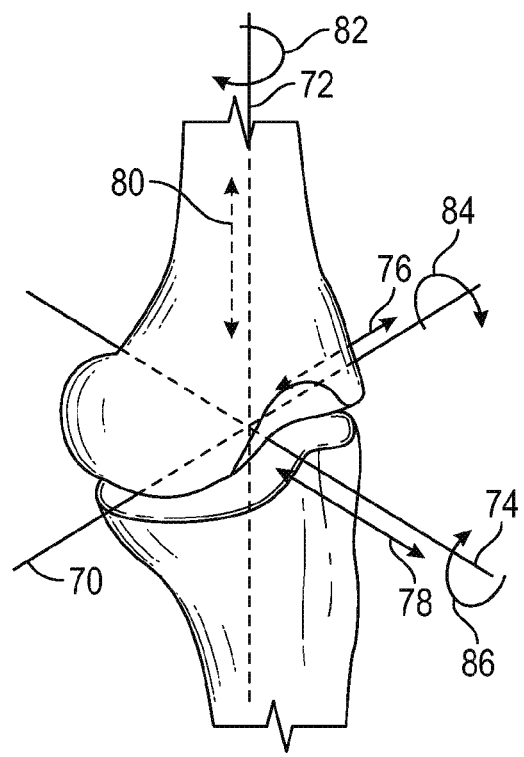
FIG. 2A is an elevated perspective view of the tibia and femur showing various axes of the knee joint according to the example of the present invention.

FIG. 2A depicts six aspects of component positioning relative to a coordinate system in which the x-axis 70 (media-lateral axis) corresponds approximately to the joint line 39, the z-axis 72 (proximal-distal axis) corresponds approximately to the mechanical axes 34 and 38, and the y-axis 74 (anterior-posterior axis) is normal to the other two. Position along each of these axes is depicted by arrows. Position along the x, y, and z axes determines the medial-lateral (dx) 76, anterior-posterior (dy) 78, and proximal-distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 2B:
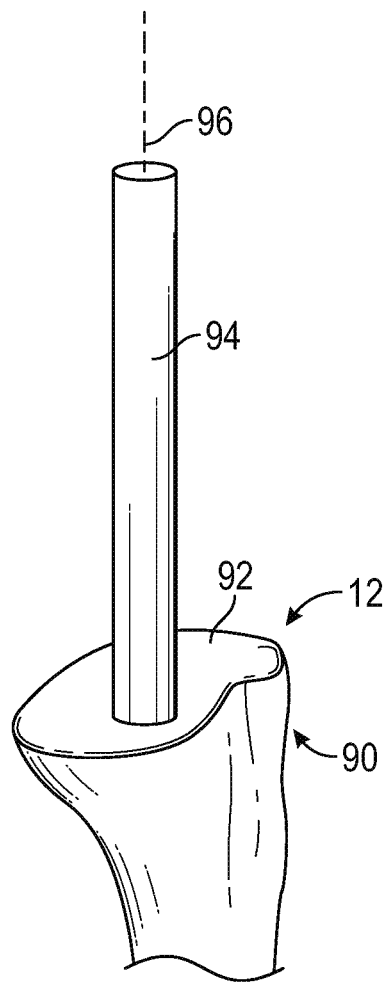
FIG. 2B is an elevated perspective view of a proximal end of the tibia having been resected for replacement of the joint surfaces according to an example of the present application.

FIG. 2B depicts a resected proximal end 90 of the tibia 12. As discussed, the proximal end 90 can have a surface 92 that has a posterior slope angle from anterior to posterior. The proximal end 90 of the tibia 12 shown in FIG. 2B has additionally been reamed or otherwise had the bone removed to form an aperture (not shown) that generally aligns with the intramedullary canal of the tibia 12. A rod 94 or another type of tool can extend into the intramedullary canal and can be used to carry the IM cutting rig assembly discussed in reference to the subsequent FIGURES. More particularly, the rod 94 can extend from the intramedullary canal and from tibia 12 along axis 96 (corresponding to z-axis 72 and the mechanical axis 38). The rod 94 can be configured to couple with a boom assembly of the IM cutting rig assembly in order to mount the LM cutting rig assembly relative to the tibia 12 for use.

FIGS. 3A to 3D show an IM cutting rig assembly 110, referred to simply as the assembly 110 hereinafter, according to an example of the present application. The assembly 110 can be mounted to the tibia 12 (FIG. 2B) via the rod 94 in a manner discussed subsequently. The assembly 110 can be configured to connect to and orient a tibial cut guide (not shown) relative to the tibia 12 in a manner discussed herein. The assembly 110 can include a adjustment member 112, a carrier assembly 114, a posterior slope housing assembly 116, and a boom assembly 118.

The adjustment member 112 can comprise a T-shaped rod 120 having threading 122 (FIG. 3C) along at least one surface according to the example of FIGS. 3A to 3D. The adjustment member 112 can be configured to couple with both the carrier assembly 114 and the posterior slope housing assembly 116. The carrier assembly 114 can be configured to couple with the tibial cut guide (not shown) and can be configured to facilitate adjustment of the tibial cut guide along the adjustment member 112. More particularly, the carrier assembly 114 can be configured to selectively couple with the adjustment member 112 such that the carrier assembly 114 is moveable relative to the adjustment member 112 to a desired position. Thus, the adjustment member 112 can provide a track along which the carrier assembly 114 can move in a proximal-distal direction.

The posterior slope housing assembly 116 can be connected to the adjustment member 112 and can be configured to pivot the adjustment member 112 relative to at least a portion of the posterior slope housing 116, the boom assembly 118 and the tibia 12. More particularly, the adjustment member 112 can include a proximal end portion 124. The proximal end portion 124 posterior slope housing assembly 116 can be pivotally connected via pin 126 to the posterior slope housing assembly 116. The posterior slope housing assembly 116 can have a slot or opening that allows the adjustment member 112 to pivot outward therefrom (e.g., toward or away from the axis 96 in FIGS. 3A and 3B). Therefore, the posterior slope housing assembly 116 can be configured for pivot connection to the adjustment member 112 according to some examples. Furthermore, the posterior slope housing assembly 116 can be configured to pivot the adjustment member 112 relative to at least a portion of the posterior slope housing assembly 116, the boom assembly 118 and the tibia 12 to adjust a posterior slope angle defined by the tibial cut guide.

The boom assembly 118 can be configured to couple with the posterior slope housing assembly 116 and can be configured to couple with a tool (e.g., tool 94 of FIG. 2B) that is insertable into the intramedullary canal of the tibia. Such coupling can be achieved by a collet or another type of mechanical connection known in the art. Thus, when assembled, the boom assembly 118 can be coupled with the posterior slope housing assembly 116 and can be configured to couple with the tool that is insertable into the intramedullary canal of the tibia. The boom assembly 118 can be configured to provide a track for anterior-posterior movement of the posterior slope housing assembly 116 relative thereto.

The assembly 110 can be used to quickly and accurately position (with regard to proximal-distal location, anterior-posterior location, and/or posterior slope angle) the tibial cut guide for removal of the articular surfaces of the tibia. The assembly 110 can include components such as the posterior slope housing assembly 116 that can quickly and accurately adjust the posterior slope angle and/or anterior-posterior position of the tibia cut guide. Furthermore, the carrier assembly 114 can be used in combination with the adjustment member 112 to adjust the proximal-distal position of the tibial cut guide and can be configured to allow for coupling of the tibial cut guide with the carrier assembly 114 in a quick and efficient manner. According to further examples, the posterior slope housing assembly 116 can be configured to allow for adjustment of the posterior slope angle of the tibial cut guide relative to the tibia without having to swap out the tibial cut guide for another tibial cut guide (e.g., swap a cut guide with a cut slot predefining 3° of posterior slope angle for a cut guide with a cut slot predefining 5° of posterior slope angle). Thus, only one tibial cut guide need be utilized with the assembly 110. Additionally, the posterior slope housing assembly 116 can be configured to allow for non-discrete (non-incremental) adjustment of the posterior slope angle of the tibial cut guide relative to the tibia. This allows for smooth and continuous adjustment and can allow for virtually any desired posterior slope angle (e.g., 2°, 2.1°, 2.2°, and so forth) to be achieved. Thus, the assembly 110 can allow resection of the tibia to be performed with minimal amounts of adjustment and/or swapping of the tibial cut guide.

Figure 4A:
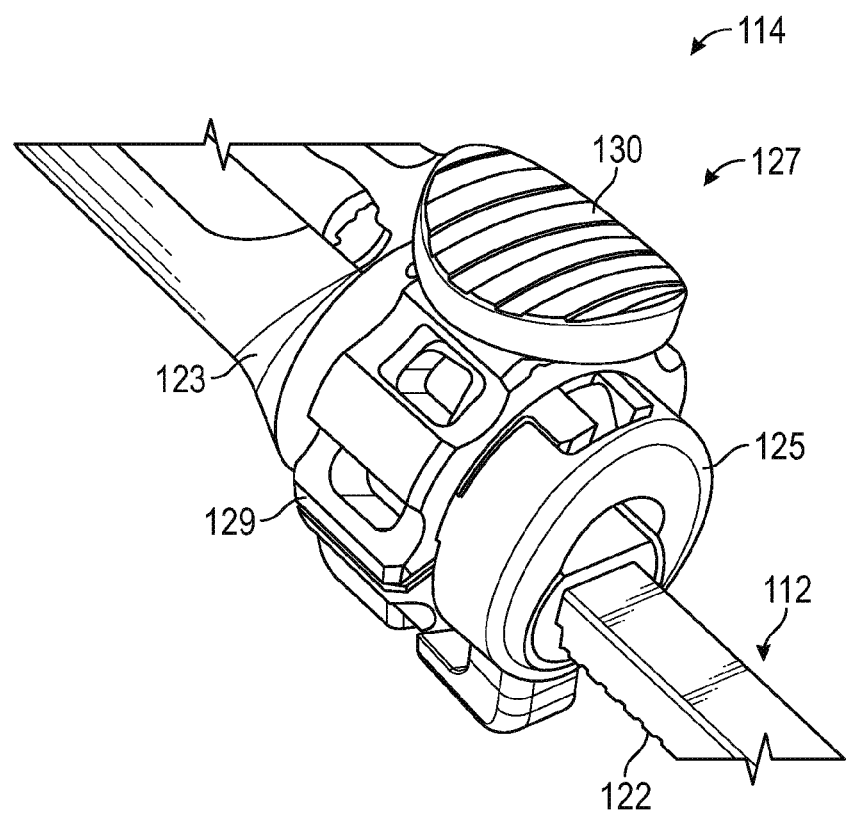
FIG. 4A is a perspective view of an engagement mechanism of a carrier assembly of the IM cutting rig assembly of FIGS. 3A-3D according to an example of the present application.
Figure 4B:
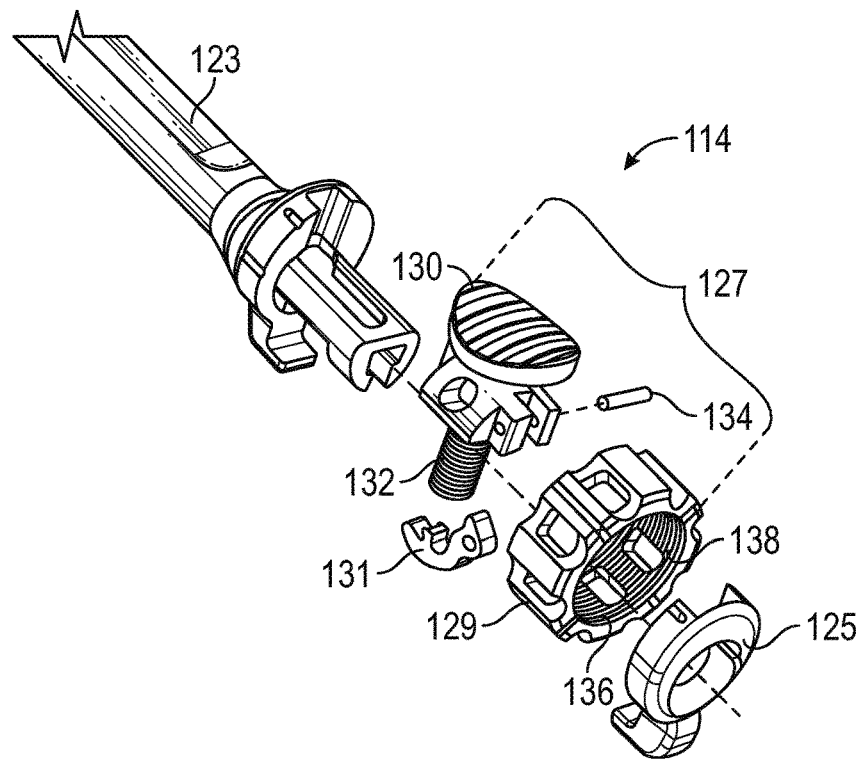
FIG. 4B is an exploded view of the engagement mechanism of the carrier assembly of FIG. 4A according to an example of the present application.

FIGS. 4A and 4B illustrate a distal portion of the carrier assembly 114, and FIG. 4A additionally shows a portion of the adjustment member 112 according to one example. FIG. 4A shows the carrier assembly 114 coupled with the adjustment member 112. FIG. 4B shows an exploded view of the carrier assembly 114. The carrier assembly 114 can include a carrier housing 123, a bottom cap 125, and an engagement mechanism 127. As shown in FIG. 4B, the engagement mechanism 127 can include a knob 129, a button 130, a lever 131, a spring 132, and a pin 134. The knob 129 can additionally include threading 136 along an interior surface 138 thereof.

As shown assembled in FIG. 4A, the carrier housing 123 can be configured to receive the adjustment member 112. The knob 129 and button 130 can be moved toward or away from a long axis of the carrier housing 123 and the adjustment member 112. The knob 129 can be rotatable relative to the button 130, the housing 120, the adjustment member 112 and other components of the carrier assembly 114. The knob 129 can be distal of and can be moved/translated inward of portions of the button 130 (e.g., can be surrounded on both an interior and exterior by the button in some locations). The bottom cap 125 can be configured to interface with the button 130 and knob 129 at a distal end.

The button 130 can connect to the lever 131 via the pin 134 and can extend both externally to and internally within the knob 129. The spring 132 can be positioned within the knob 129 between the internal portions of the button 130 and a non-threaded portion of the adjustment member 112. According to the example shown, the spring 132 can be captured between the button 130 and the lever 131. Thus, the button 130 and lever 131 can be configured to receive and retain the spring 132. The spring 132 can exert a compressive force against the knob 129, via the button 130, and the knob 129 can in turn engage the adjustment member 112 such that threading 122 of the adjustment member 112 engages threading 136 of the knob 129.

The button 130 can be depressed such that the knob 129 becomes loose (i.e. a gap opens between threading 122 and threading 136 as the force of the spring 132 is removed) laterally relative to the adjustment member 112. Non-engagement between the knob 129 and the adjustment member 112 allows the carrier assembly 114 to be moved relative to the adjustment member 112. The non-engagement between the knob 129 and the adjustment member 112 can also facilitate quick assembly of the carrier assembly 114 onto the adjustment member 112 in some cases. Upon release of the button 130, the force of the spring 132 can push the knob 129 back into engagement with the adjustment member 112 (i.e., the treading 122 can engage the treading 136). This action can lock the position of the carrier assembly 114 relative to the adjustment member 112. According to some examples, turning of the knob 129 can permit adjustment of the position of the carrier assembly 114 relative to the adjustment member 112 (e.g., threading 122, 136 can be configured for axial advancement). The pin 134 can prevent disassembly of the button 130, the lever 131, and the spring 132.

The knob 129 can be translated radially to engage the threading 122 of the adjustment member 112, and the button 130 can be configured to be actuated (moved inward or outward) to overcome the force of the spring 132 to facilitate movement of the carrier assembly 114 along the adjustment member 112. Therefore, the knob 129 can be pushed radially via button 130, lever 131, and spring 132, to engage its inner threading 136 with the threading 122 of the adjustment member 112. The button 130 can be configured to be actuated to translate the knob 129 radially to disengage threading 122 and 136 to facilitate the movement of the carrier assembly 114 along the adjustment member 112.

Figure 3A:
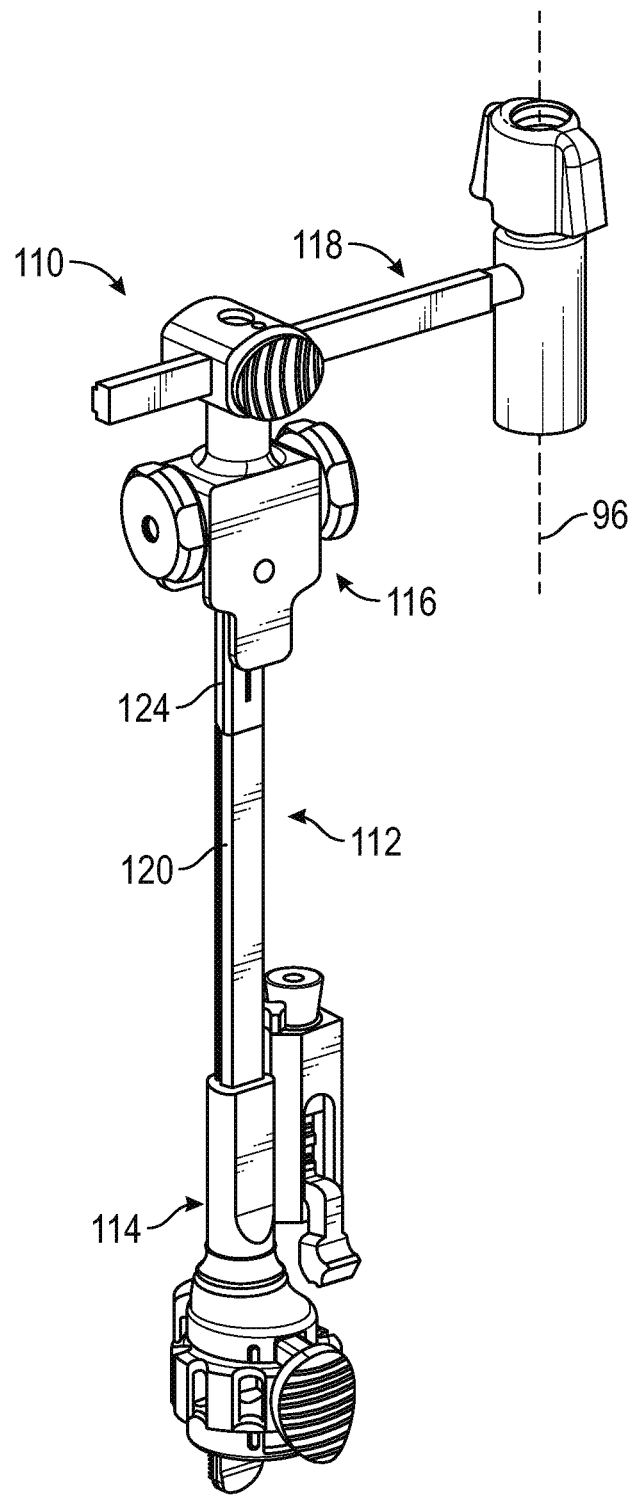
FIG. 3A is a perspective view of an intramedullary (IM) cutting rig assembly according to an example of the present invention.
Figure 3B:
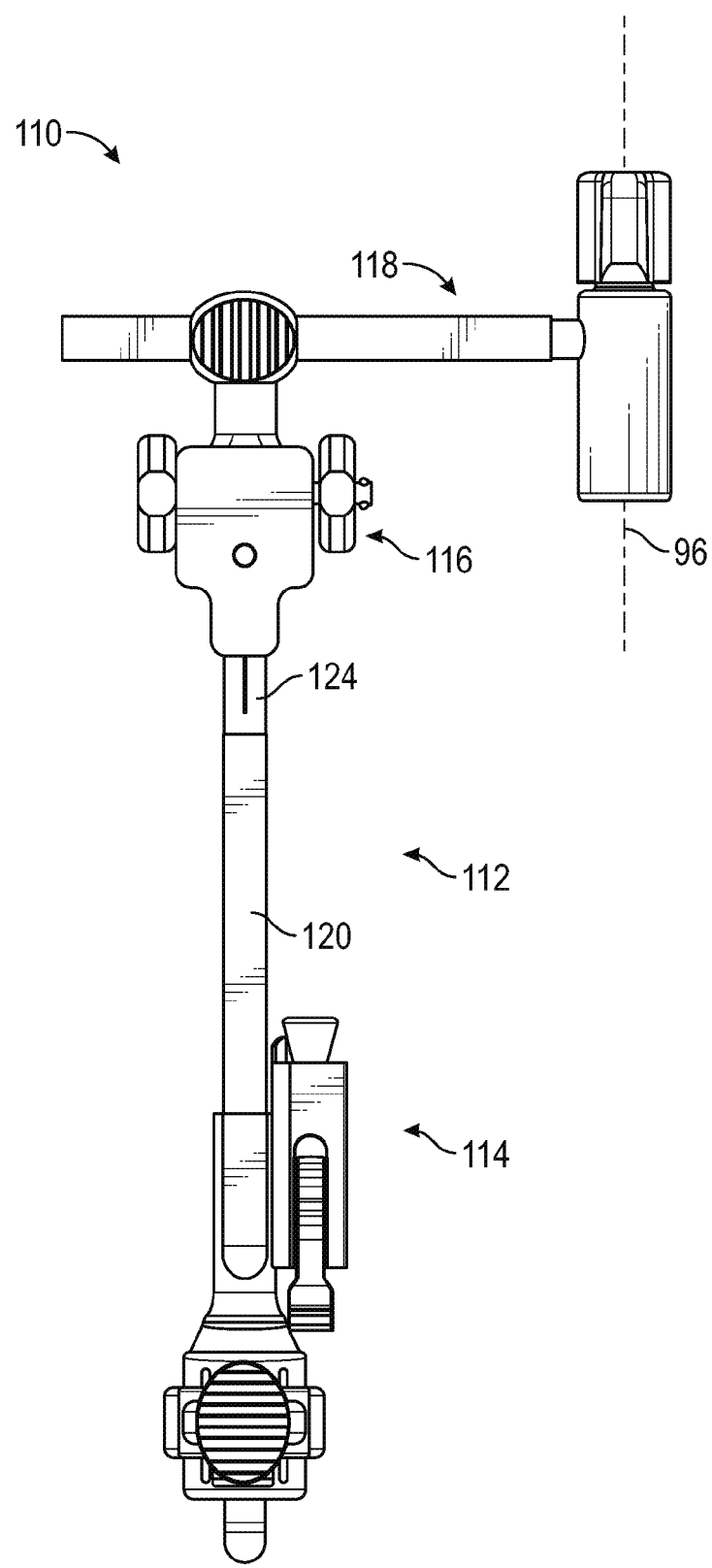
FIG. 3B is a side view of the IM cutting rig assembly of FIG. 3A according to an example of the present application.
Figure 3C:
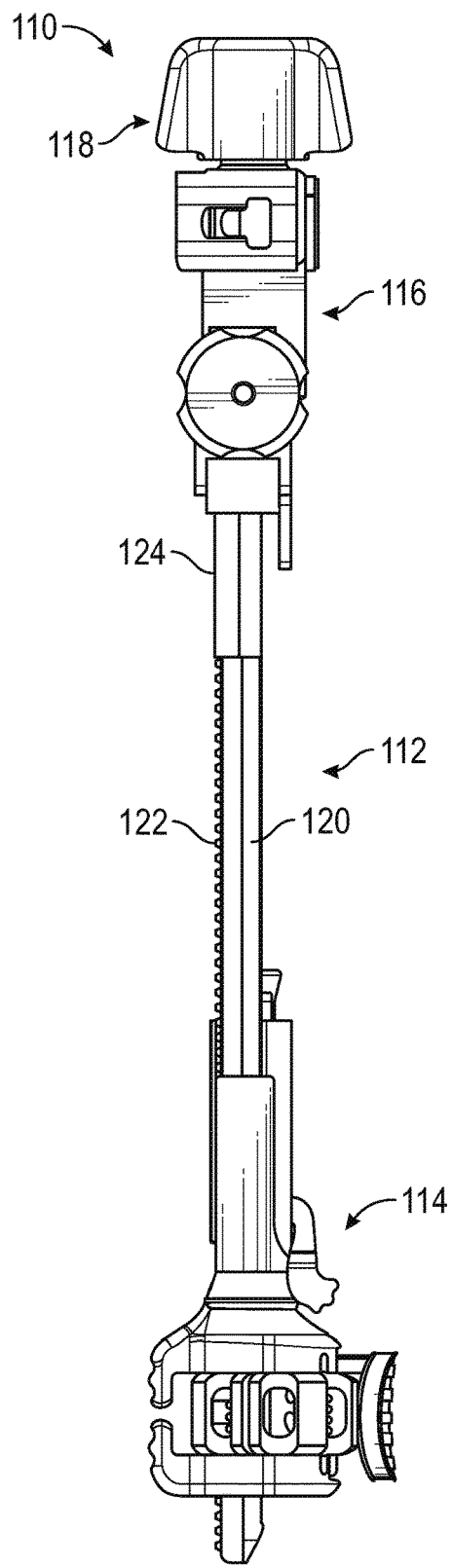
FIG. 3C is a plan view of an anterior side of the IM cutting rig assembly of FIG. 3A according to an example of the present application.
Figure 3D:
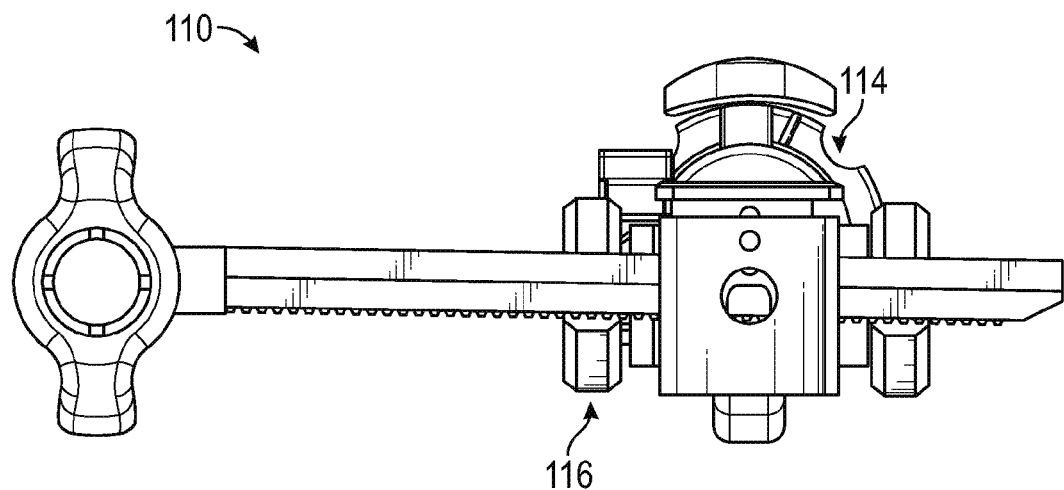
FIG. 3D is a plan view of a proximal side of the IM cutting rig assembly of FIG. 3A according to an example of the present application.
Figure 5A:
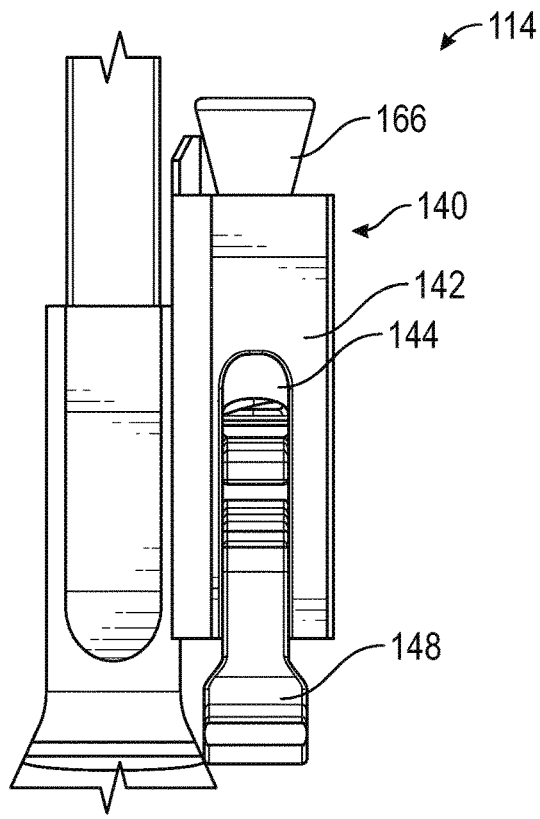
FIG. 5A is a perspective view of a tibial cut guide locking mechanism of the carrier assembly of the IM cutting rig assembly of FIGS. 3A-3D according to an example of the present application.
Figure 5B:
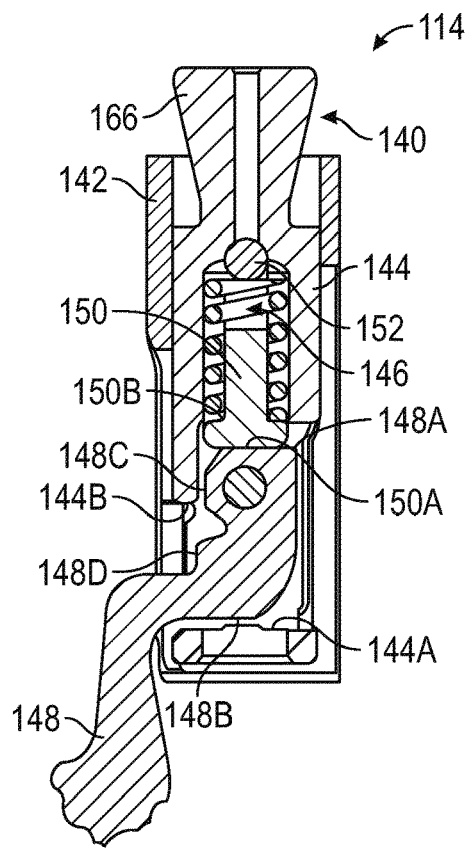
FIG. 5B is a cross-sectional view of the tibial cut guide locking mechanism of the carrier assembly of FIG. 5A according to an example of the present application.
Figure 5C:
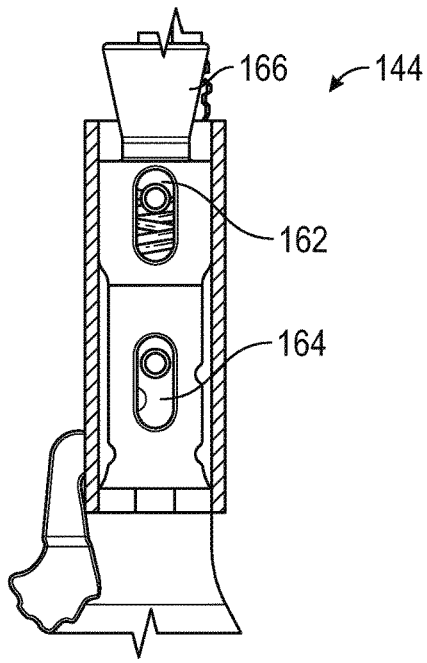
FIG. 5C is a plan view with portions of a housing removed to illustrate a body component residing therein according to an example of the present application.
Figure 5D:
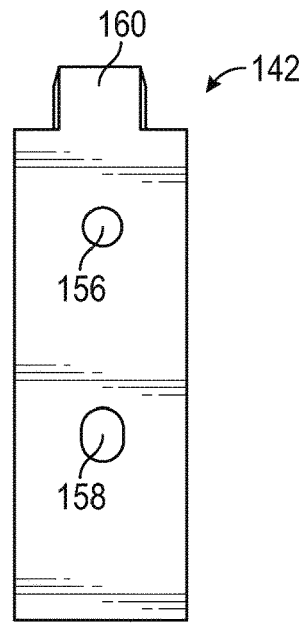
FIG. 5D is a plan view of a portion of the housing of the tibial cut guide locking mechanism of FIGS. 5A to 5C according to an example of the present application.

FIGS. 5A to 5D illustrate further portions and components of the carrier assembly 114 that can be used to couple the tibial cut guide to the remainder of the assembly 110 (FIGS. 3A to 3C). As shown in FIGS. 5A to 5D, the carrier assembly 114 can include a tibial cut guide locking mechanism 140. The tibial cut guide locking mechanism 140 can include a housing 142, a body component 144, a spring 146 (FIGS. 5B, 5C), a lever 148 (FIGS. 5A, 5B, 5C), a member 150 (FIG. 5B) and first and second pins 152, 154 (FIG. 5B, 5C). The housing 142 can include first aperture 156 and a slot 158 and a projection 160 as shown in FIG. 5D. The body component 144 can include first and second slots 162, 164 as shown in FIG. 5C.

The housing 142 can comprise a hollow containment member having openings at both the proximal end and a distal side thereof. The body component 144 can reside therein, and can have a conic head portion 166 that extends therefrom on a proximal end. As will be discussed, the body component 144 can be moveable relative to the housing 142 in a constrained manner. The spring 146 can be positioned within the body component 144 (between the first pin 152 and an inferior surface 150B (FIG. 5B) of a head of the member 150). The member 150 can be contacted on the superior surface 150A. (FIG. 5B) of the head by the surfaces 148A or 148C (FIG. 5B) of lever 148. The lever 148 can extend from the distal side opening of the housing 142 and a distal side opening of the body component 144 as shown in FIGS. 5A and 5B. The first pin 152 can be received in the first aperture 156 of the housing 142 and can be received in the first slot 162 of the body component 144. The second pin 154 can be received in the slot 158 of the housing 142 and can be received in the second slot 164 of the body component 144.

In operation, the lever 148 can be actuated upward (pivoting about the second pin 154) away from the position shown in FIGS. 5A-5D to unlock the tibial cut guide locking mechanism 140 to facilitate removal of and/or addition of the tibial cut guide, which is mounted to the conic head portion 166. Movement of the lever 148 can allow the body component 144 to be translated upward relative to the housing 142 (the first and second slots 162, 164 of the body component 144 can facilitate translation of the body component 144 relative to the first and second pins 152, 154). The surface 148C of the lever 148 can come in contact with surface 150A of component 150 while surface 148D comes in contact with surface 144B (FIG. 5B) to push component 144 upward/proximally. The spring 146 is not constrained until the second pin 154 contacts the proximal end of the slot 158 in the housing 142. With movement of the body component 144 proximally, the conic head portion 166 has sufficient clearance relative to a proximal end portion of the housing 142 such that a mating female conic portion of the tibial cut guide can be mounted to the body component 144 and the housing 142. When the lever is pivoted back to the distal position illustrated in FIGS. 5A to 5D, surface 148B can come in contact with the surface 144A at the bottom of the inner cavity of component 144 which can move distally. Surface 150A of component 150 can come in contact with surface 148A of the lever 148 that is thus maintained in a distal position. In the distal position, a conic lock between the cut guide and the conical head portion 166 is maintained by the spring 146 such that the male conic portion 166 is in fully engaged contact and is seated with the female conic portion located on the tibial cut guide. The projection 160 extending proximally from the proximal end of the housing 142 can be configured to fit in a female counterpart slot or recess in the tibial cut guide. In this manner, the body component 144 and the housing 142 (via projection 160) can constrain the proximal-distal and rotational movement of the tibial cut guide with respect to the earlier assembly 114. Further disclosure of tibial cut guides and their coupling to alignment guides using conic features is described in United States Application Publication 2013/0204260, the entire disclosure of which is incorporated herein for reference.

Figure 6A:
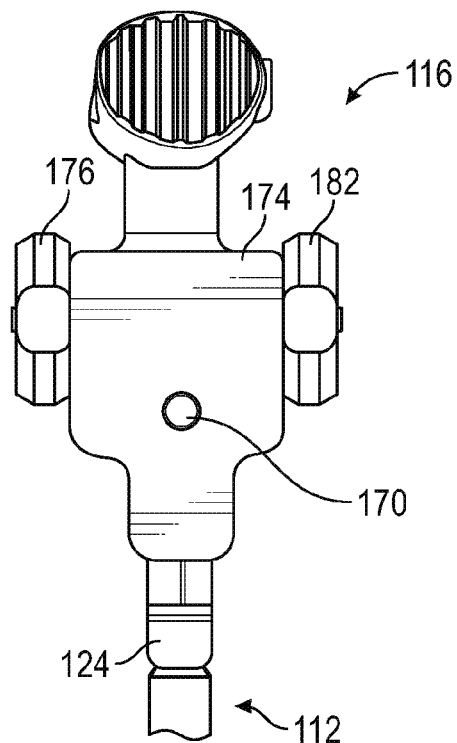
FIG. 6A is a view of a posterior slope housing assembly of the IM cutting rig assembly of FIGS. 3A-3D according to an example of the present application.
Figure 6B:
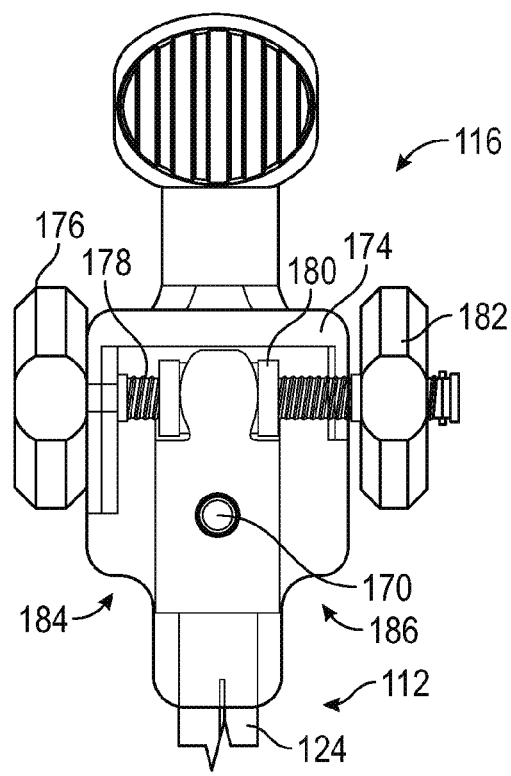
FIG. 6B is a view of the posterior slope housing assembly of FIG. 4A with components illustrated in phantom according to an example of the present application.
Figure 6C:
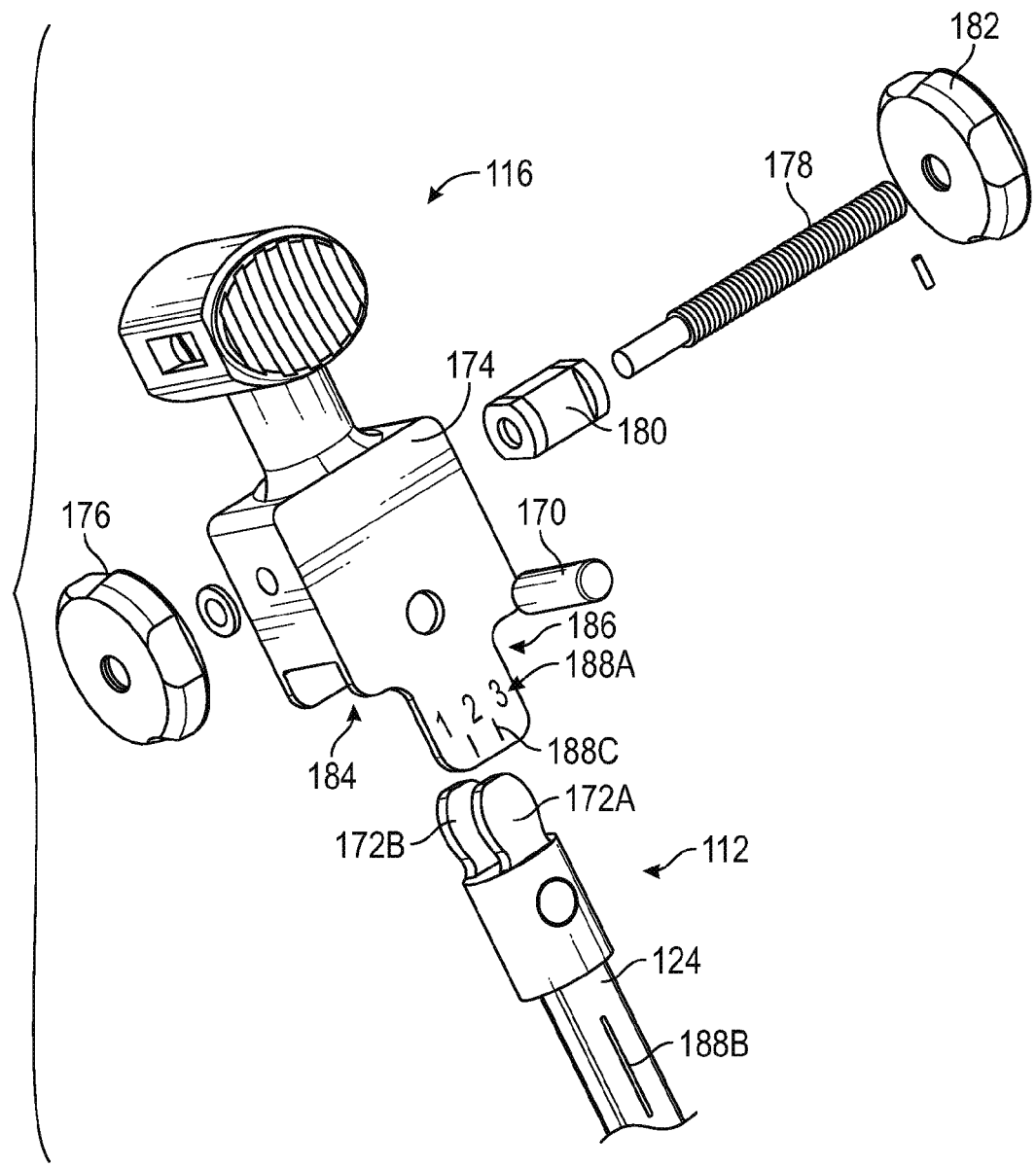
FIG. 6C is an exploded view of the posterior slope housing assembly of FIG. 4A according to an example of the present application.

FIGS. 6A to 6C show the posterior slope housing assembly 116 according to one example. The posterior slope housing assembly 116 is shown assembled in FIGS. 6A and 6B and disassembled in FIG. 6C. The proximal end portion 124 of the adjustment member 112 is illustrated in FIGS. 6A to 6C along with a hinging pin 170 that facilitates a pivot connection between the posterior slope housing assembly 116 and the adjustment member 112. The proximal end portion 124 can include projections 172A, 172B (FIG. 6C) that can facilitate pivoting actuation of the adjustment member 112 via linear movement of components of the posterior slope housing assembly 116 in a manner to be described subsequently.

The posterior slope housing assembly 116 can include a housing 174, an actuation knob 176, a screw 178 (FIGS. 6B, 6C), a key connector 180 (FIGS. 6B, 6C), and a counter-nut 182. The housing 174 includes an open distal portion including anterior opening 184 (FIGS. 6B, 6C) and posterior opening 186 (FIGS. 6B, 6C).

The hinging pin 170 can pivotally connect the adjustment member 112 to the posterior slope housing assembly 116. The housing 174 can be configured with a hollow interior and open distal portion to facilitate insertion of the proximal end portion 124 of the adjustment member 112 into the posterior slope housing assembly 116. The knob 176 can be positioned at an anterior portion of the housing 174 proximal of the hinging pin 170. The knob 176 can be coupled to rotate the screw 178. The screw 178 extends through the housing 174 and can be connected to the counter-nut 182 which is positioned at a posterior portion of the housing 174. The key connector 180 can be received within the housing 174 such as within a generally linear extending passage and can be moved by rotation of the screw 178. The key connector 180 can be configured to couple with and actuate the adjustment member 112 to pivot about hinging pin 170. In particular, the projections 172A and 172B can be configured to capture the key connector 180 therebetween (and indeed can be captured by mating features such as recesses in the key connector 180). The projections 172A and 172B can be sized to facilitate some degree of movement of the proximal end portion 124 relative to the key connector 180 to facilitate pivoting.

In one example, the knob 176 can be rotated relative to the housing 174 to rotate the screw 178. Rotation of the screw 178 can cause translation of the key connector 180 which in turn can cause the rotation of adjustment member 112 (i.e. the key connector 180 can be configured to translate relative to the screw 178 and housing 174 to move the proximal end portion 124 of the adjustment member 112 and facilitate pivoting of the adjustment member 112 relative to the tibia to adjust the posterior slope angle defined by the tibial cut guide. The screw 178 and the key connector 180 can be configured such that rotation of the screw 178 and translation of the key connector 180 can facilitate a non-discrete adjustment of the posterior slope angle via smooth pivoting of the adjustment member 112. Pivoting of the adjustment member 112 relative the housing 174 can cause the adjustment member 112 to exit from one of the anterior opening 184 and posterior opening 186 of the housing 174.

In some examples, the counter-nut 182 can be configured to engage the housing 174 to lock a position of the screw 178 and the key connector 180 (and hence, the adjustment member 112). The housing 174 and adjustment member 112 can include visual indicia 188A and 188B including incremental value indicia of less than 1° 188C indicating the posterior slope angle.

Figure 7A:
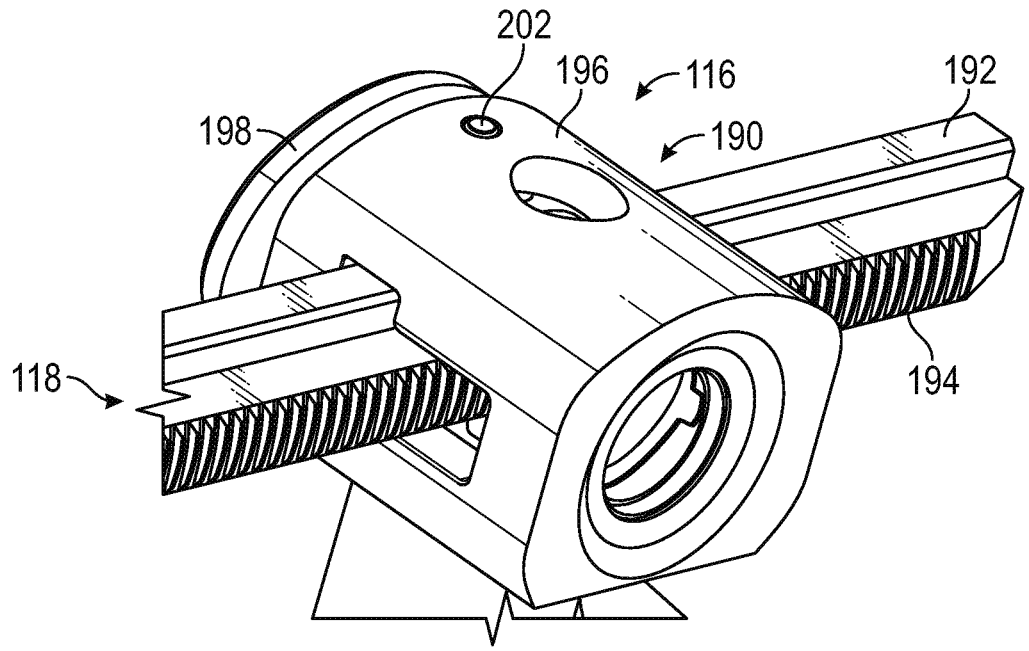
FIG. 7A is a perspective view of an adjustment mechanism of the posterior slope housing assembly of FIGS. 3A-3D according to an example of the present application.
Figure 7B:
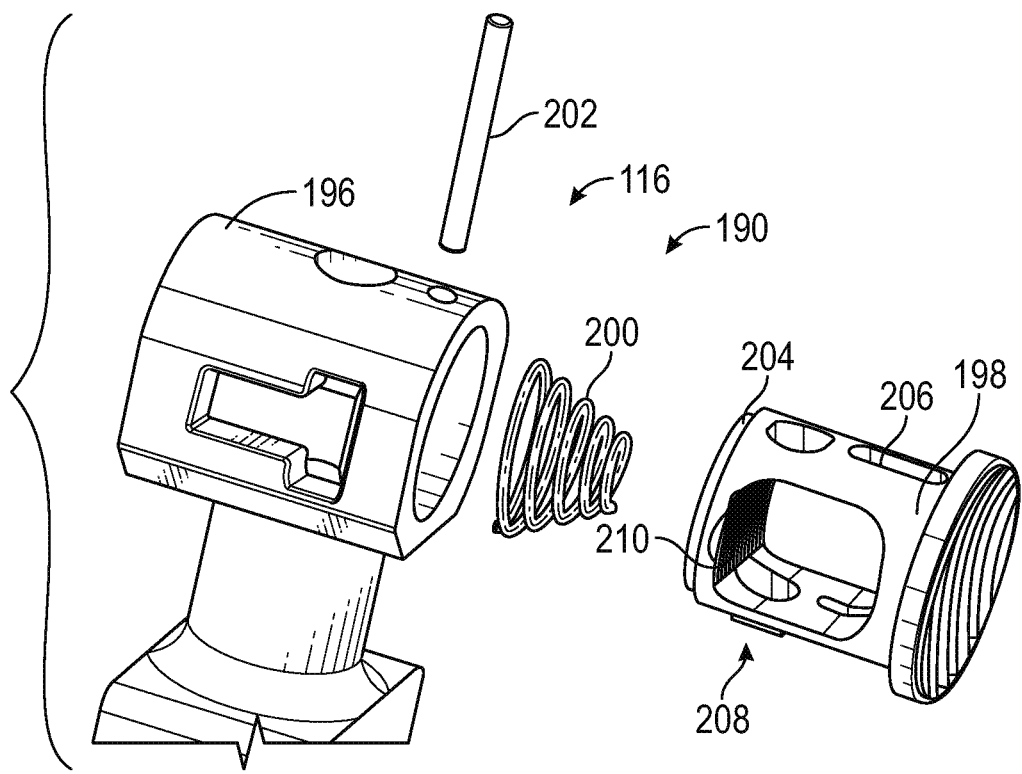
FIG. 7B is an exploded view of the adjustment mechanism of FIG. 7A according to an example of the present application.

FIGS. 7A and 7B show an adjustment mechanism 190 of the posterior slope housing assembly 116 according to an example of the present application. FIG. 7A illustrates the adjustment mechanism 190 can facilitate coupling with the boom assembly 118. As shown in FIG. 7A, the boom assembly 118 can comprise a T-shaped rod 192 having threading 194 along one surface thereof. As shown in FIGS. 7A and 7B, the adjustment mechanism 190 can include a housing 196, a button 198, a spring 200 (FIG. 7B), and a pin 202.

The housing 196 can be configured to receive the T-shaped rod 192 therethrough. Similarly, the housing 196 includes an open end and is configured to receive a portion of the button 198 therein. The spring 200 (e.g., a conical compression spring) can be positioned between an end portion 204 (FIG. 7B) of the button 198 and an interior bottom surface of the housing 196. When assembled as shown in FIG. 7A, the pin 202 can be received in apertures in the housing 196 (only one is shown) and can additionally be received in a slot 206 (FIG. 7B) in the button 198. The button 198 can include a passage 208 (FIG. 7B) configured to allow the T-shaped rod 192 to extend therethrough. An interior of the passage 208 can be provided with threading 210 configured to engage with the threading 194 of the T-shaped rod 192.

When the button 198 is actuated, the posterior slope housing assembly 116 can move along the T-shaped rod 192 of the boom assembly 118 generally in an anterior-posterior direction relative to the knee. The configuration of the adjustment mechanism 190 can facilitate fast assembly and adjustment of the cut guide in a desired position. Upon release of the button 198, the spring 200 can push the inner threading 210 of the interior surface of the passage 208 into engaging contact with the threading 194 of the T-shaped rod 192 to lock the position of the posterior slope housing assembly 116 relative to the boom assembly 118, The pin 202 can be inserted through and welded or otherwise affixed to the housing 196 to prevent disassembly that could be caused by the action of the spring 200 on the button 198.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the follow- The claimed invention is:

1. A system for a knee replacement surgery comprising:
an adjustment member;
a carrier assembly configured to couple with a cut guide and configured to be moveable relative to the adjustment member;
a posterior slope housing assembly configured for pivot connection to the adjustment member, the posterior slope housing assembly configured to pivot the adjustment member relative to at least a portion of the posterior slope housing and a tibia to adjust a posterior slope angle defined by the cut guide, wherein the posterior slope housing assembly is pivotally connected to the adjustment member along a proximal end portion thereof, the proximal end portion configured to mate with a moveable connector of the posterior slope housing assembly, and wherein the posterior slope housing assembly includes a knob configured to rotate a screw, and the connector is configured to translate on the screw to rotate the proximal end portion of the adjustment member and facilitate pivoting of the adjustment member relative to the tibia to adjust the posterior slope angle; and
a boom configured to couple with the posterior slope housing assembly and configured to couple with a tool that is insertable into an intramedullary canal of the tibia.

2. The system of claim 1, wherein the adjustment member comprises a T-shaped rod having threading along at least one surface thereof, and wherein the carrier assembly includes an engagement mechanism comprising a threaded knob configured to selectively engage the threading.

3. The system of claim 2, wherein the threaded knob is displaced via a spring force to engage the threading, and the engagement mechanism includes a button configured to be actuated to overcome the spring force and facilitate movement of the carrier assembly along the adjustment member.

4. The system of claim 1, wherein the carrier assembly includes a body component moveable relative to a housing, the body component configured to engage with the cut guide, and wherein the carrier assembly includes a mechanism that couples and locks the body component with the housing.

5. The system of claim 1, further comprising a counter-nut configured to engage the posterior slope housing assembly to lock a position of the screw and connector, and wherein the posterior slope housing assembly and adjustment member include visual indicia including incremental value indicia down to or less than 1° indicating the posterior slope angle.

6. The system of claim 1, wherein rotation of the screw and translation of the connector facilitate a non-discrete adjustment of the posterior slope angle.

7. The system of claim 1, wherein the boom comprises a T-shaped rod having threading along at least one surface thereof, and wherein the posterior slope housing assembly includes an adjustment mechanism that comprises a button that is configured to be depressible to facilitate adjustment of the posterior slope housing assembly and releasable to engage the threading.

8. The system of claim 1, wherein the adjustment member is configured to provide a track for proximal-distal movement of the carrier assembly, and wherein the boom is configured to provide a track for anterior-posterior movement of the posterior slope housing assembly.

9. An assembly for a knee replacement surgery comprising:
an adjustment member;
a carrier assembly selectively coupled with the adjustment member such that the carrier assembly is moveable relative to the adjustment member to a desired position;
a posterior slope housing assembly connected to the adjustment member and configured to pivot the adjustment member relative to a portion of the posterior slope housing and a tibia, wherein the posterior slope housing assembly is pivotally connected to the adjustment member along a proximal end portion thereof, the proximal end portion is configured to mate with a moveable key connector of the posterior slope housing assembly, and wherein the posterior slope housing assembly rotates a screw, and the key connector translates on the screw to move the proximal end portion of the adjustment member and facilitate pivoting of the adjustment member relative to the tibia to adjust the posterior slope angle; and
a boom coupled to the posterior slope housing assembly and coupled with a mounting component to mount the posterior slope housing assembly, the carrier assembly and the adjustment member relative to the tibia.

10. The assembly of claim 9, wherein the adjustment member comprises a T-shaped rod having threading along at least one surface thereof, and wherein the carrier assembly includes an engagement mechanism that includes a threaded knob configured to selectively engage the threading.

11. The assembly of claim 10, wherein the threaded knob is displaced via a spring force to engage the threading, and the engagement mechanism includes a button that when actuated overcomes the spring force to facilitate movement of the carrier assembly along the adjustment member.

12. The assembly of claim 9, wherein the carrier assembly includes a body component moveable relative to a housing, the body component configured to engage with a cut guide to seat the cut guide, and wherein the carrier assembly includes a mechanism that couples and locks the body component with the housing.

13. The assembly of claim 9, further comprising a counter-nut configured to engage the posterior slope housing assembly to lock a position of the screw and key connector, and wherein the posterior slope housing and adjustment member include visual indicia including incremental value indicia down to or less than 1° indicating the posterior slope angle.

14. The assembly of claim 9, wherein rotation of the screw and translation of the key connector facilitate a non-discrete adjustment of the posterior slope angle.

15. The assembly of claim 9, wherein the boom comprises a T-shaped rod having threading along at least one surface thereof, and wherein the posterior slope housing assembly includes an adjustment mechanism that comprises a button that is configured to be depressible to facilitate adjustment of the posterior slope housing assembly and releasable to engage the threading.

16. The assembly of claim 9, wherein the adjustment member provides a track for proximal-distal movement of the carrier assembly, and wherein the boom provides a track for anterior-posterior movement of the posterior slope housing assembly.

* * * * *